(12) United States Patent
Hakky

(10) Patent No.: US 10,631,856 B2
(45) Date of Patent: *Apr. 28, 2020

(54) METHOD OF IMPLANTING A PENILE PROSTHESIS

(71) Applicant: Coloplast A/S, Humlebaek (DK)

(72) Inventor: Tariq Hakky, Duluth, GA (US)

(73) Assignee: Coloplast A/S, Humlebaek (DK)

(*) Notice: Subject to any disclaimer, the term of this patent is extended or adjusted under 35 U.S.C. 154(b) by 93 days.

This patent is subject to a terminal disclaimer.

(21) Appl. No.: 15/963,113

(22) Filed: Apr. 26, 2018

(65) Prior Publication Data

US 2018/0235607 A1    Aug. 23, 2018

Related U.S. Application Data

(63) Continuation of application No. 14/698,954, filed on Apr. 29, 2015, now Pat. No. 9,980,722.

(60) Provisional application No. 61/993,120, filed on May 14, 2014.

(30) Foreign Application Priority Data

Apr. 30, 2015   (EP) ..................... 15165827

(51) Int. Cl.
| | | |
|---|---|---|
| *A61F 5/00* | (2006.01) | |
| *A61B 17/06* | (2006.01) | |
| *A61B 17/04* | (2006.01) | |
| *A61B 17/34* | (2006.01) | |
| *A61F 2/26* | (2006.01) | |
| *A61B 17/00* | (2006.01) | |

(52) U.S. Cl.
CPC ........ *A61B 17/06066* (2013.01); *A61B 17/04* (2013.01); *A61B 17/06004* (2013.01); *A61B 17/06109* (2013.01); *A61B 17/3468* (2013.01); *A61B 2017/00349* (2013.01); *A61B 2017/06009* (2013.01); *A61B 2017/06052* (2013.01); *A61F 2/26* (2013.01)

(58) Field of Classification Search
CPC ................. A61F 2/26; A61B 17/04; A61B 17/06; A61B 17/06066; A61B 17/06004; A61B 17/06109
USPC ...................................... 600/38–41
See application file for complete search history.

(56) References Cited

U.S. PATENT DOCUMENTS

| | | | |
|---|---|---|---|
| 4,244,370 A * | 1/1981 | Furlow | A61F 2/26 128/DIG. 20 |
| 9,980,722 B2 * | 5/2018 | Hakky | A61B 17/06066 |
| 2004/0015177 A1 * | 1/2004 | Chu | A61B 17/0469 606/139 |

(Continued)

*Primary Examiner* — John P Lacyk
(74) *Attorney, Agent, or Firm* — Coloplast Corp., Coloplast A/S; Nick Baumann

(57) ABSTRACT

A method of implanting a penile prosthesis includes providing a tool including a needle having a locking groove formed in a shaft of the needle, where the locking groove has a ridge or a notch. The method includes accessing a penile implant having a length of suture coupled to a distal end of the penile implant, securing the length of suture into the locking groove of the needle; inserting the tool and the needle into a corpora cavernosum of a penis; passing the needle and the length of suture through a glans of the penis; disengaging the length of suture from the locking groove of the needle; and pulling the penile implant into the corpora cavernosum of the penis with the length of suture.

18 Claims, 11 Drawing Sheets

(56) References Cited

U.S. PATENT DOCUMENTS

2005/0075534 A1* 4/2005 Kuyava .................. A61F 2/26
600/38

* cited by examiner

METHOD OF IMPLANTING A PENILE PROSTHESIS

CROSS REFERENCE TO RELATED APPLICATIONS

This application is a continuation of Ser. No. 14/698,954 filed on Apr. 29, 2015 which claims benefit under 35 U.S.C. § 119(e) to U.S. Ser. No. 61/993,120, filed May 14, 2014, the contents of both of which are incorporated herein by reference in their entirety.

FIELD OF THE INVENTION

The invention relates generally to penile prosthesis implantation using a locking needle.

BACKGROUND OF THE INVENTION

A penile prosthetic typically includes non-inflatable semi-rigid cylinders that are implanted in the corpora cavernosa of the penis. An inflatable penile prosthetic generally includes a liquid reservoir implanted in the abdomen that communicates with the cylinders, and a pump, often located in the scrotum, that is employed to move liquid from the liquid reservoir into the cylinders.

In a typical inflatable application, the user squeezes a bulb of the pump multiple times to incrementally draw liquid out of the liquid reservoir, into the bulb, and eventually into the cylinders. The repeated squeezing of the bulb moves the liquid from the reservoir into the cylinders, which incrementally deflates the reservoir and incrementally inflates the cylinders to eventually provide the user with an erect penis. The user may return the penis to its flaccid state by selectively transferring the liquid from the cylinders back into the reservoir.

Penile prosthesis is an invasive treatment that requires a delicate and often painful implant to surgically install. To reach the corpus cavernosa and implant the cylinders, the surgeon will first make an incision at the base of the penis, such as where it meets the scrotum. The patient is prepared for the cylinder after the surgeon has dilated each corpus cavernosum to create space for the cylinders.

Once the patient has been prepared, the surgeon will insert a medical device known as a Furlow insertion tool (U.S. Pat. No. 4,244,370) containing a Keith needle into the dilated corpus cavernosum. The Furlow insertion tool is a long slender device having a hollow barrel with a obturator at the rearward end. A Keith needle is used in many areas of medicine having a design much like that of a heavy straight sewing needle used to pierce tissue. The Keith needle fits within the bore of the Furlow insertion tool's barrel and is ejected from the forward end with the obturator.

In order to install the implant, the Keith needle is tethered to the implantable cylinder by a suture. The current prosthesis procedure, for example, as described in U.S. Pat. Pub. No. 20040167574, requires the threading of two ends of the suture through the eye of the Keith needle and manipulation of the resulting free ends of the suture before and during installation of the implant. This can be cumbersome and decrease the overall efficiency of the procedure.

Thus, there is a need for a solution that effectively alleviates the current problems associated with the implantation of inflatable penile prosthesis.

BRIEF SUMMARY OF THE INVENTION

Solutions to problems associated with penile prosthesis implantation have been discovered. The present disclosure provides a locking needle for use in a Furlow insertion tool during implantation of penile prosthesis.

In a single embodiment the disclosure provides a locking needle for the implementation of a penile prosthesis cylinder, the locking needle adapted for insertion into a Furlow insertion tool, wherein the needle contains a locking groove, and wherein a continuous suture loop can engage the graduated groove of the needle and become locked. In some aspects the graduated groove of the locking needle can secure the continuous suture loop by the use of a detachable sleeve that covers and secures the suture in the graduated groove, by a forward or rearward opening gate (that fits over the groove), and/or by a ridge or notch within the graduated groove. In one embodiment, the sleeve should be slidable or could be screwed around the shaft of the needle so that the interaction between the sleeve and shaft of the needle is tight but can still be slid along the shaft surface. In one aspect, the sleeve is of tubular form and can be threaded so that the sleeve fits along a portion or along the entire shaft of the needle. Where the sleeve is threaded, the needle shaft would also be threaded opposite to that of the thread of the sleeve so as to secure the sleeve to the needle shaft. The continuous suture which is also tethered to the cylinder of the penile prosthesis to be implanted eliminates the need to thread two suture ends through a Keith needle and fumbling with the suture ends during surgery.

In another embodiment the disclosure provides a surgical tool for the implementation of a penile prosthesis cylinder that includes a locking needle and a Furlow insertion tool. The surgical tool is used for the implementation of a penile prosthesis cylinder. The locking needle is provided within the barrel of the Furlow insertion tool, wherein the locking needle contains a graduated groove, and wherein a continuous suture loop can engage the graduated groove of the locking needle and become affixed thereto, e.g., locked. In some aspects the graduated groove of the locking needle can secure the continuous suture loop by the use of a detachable sleeve, a forward or rearward opening gate, and/or by a ridge or notch within the graduated groove. The continuous suture which is also tethered to the penile prosthesis cylinder to be implanted eliminates the need to thread two suture ends through a Keith needle and fumbling with the suture ends during surgery.

The locking needle of the current embodiments can be constructed of an alloy including titanium, chromium, nickel, cobalt, molybdenum, or combinations thereof, and also contain a suitable stabilizer including aluminum, gallium, germanium, carbon, oxygen, nitrogen, molybdenum, vanadium, tantalum, niobium, manganese, iron, chromium, cobalt, nickel, copper, silicon, or combinations thereof.

Disclosed are methods to implant a cylinder during penile prosthesis using a locking needle, the method can include (a) threading a suture through the distal end of the cylinder and securing the two ends of the suture together to form a continuous suture loop; (b) securing the continuous suture loop to the locking needle; (c) inserting the locking needle into a Furlow insertion tool; (d) inserting the Furlow insertion tool containing locking needle into the corpus cavernosum; (e) positioning the locking needle through the glans of the penis and withdrawing the Furlow insertion tool from the corpus cavernosum; (f) manipulating the locking needle and continuous suture loop and pulling the cylinder into the corpus cavernosum; and (g) cutting the continuous suture loop and removing the cut suture from the glands of the penis. Step (b) and step (c) can be reversed where the Furlow insertion tool is preloaded with the locking needle.

Also disclosed are methods to employ a surgical tool during the implantation of a penile prosthesis cylinder, the method can include (a) threading a suture through the distal end of the cylinder and securing the two ends of the suture together to form a continuous suture loop; (b) securing the continuous suture loop to the locking needle; (c) inserting the locking needle into a Furlow insertion tool; (d) inserting the surgical tool into the corpus cavernosum; (e) positioning the locking needle through the glans of the penis and withdrawing the Furlow insertion tool from the corpus cavernosum; (f) manipulating the locking needle and continuous suture loop and pulling the cylinder into the corpus cavernosum; and (g) cutting the continuous suture loop and removing the cut suture from the glans of the penis. Step (c) can be omitted where the surgical tool is preloaded with the locking needle. In one aspect, the locking needle of the preloaded surgical tool includes a forward opening gate.

Disclosed are kits to implant a penile prosthesis cylinder using the locking needle, the kit including (a) a locking needle; (b) instructions for using the kit and/or locking needle; and optional sutures.

Also disclosed are kits to implant a penile prosthesis cylinder using the surgical tool, the kit including (a) a Furlow insertion tool; (b) a locking needle; (c) instructions for using the kit and/or surgical tool; and optional sutures.

While multiple embodiments are disclosed, still other embodiments of the present invention will become apparent to those skilled in the art from the following detailed description. As will be apparent, the invention is capable of modifications in various obvious aspects, all without departing from the spirit and scope of the present invention. Accordingly, the detailed descriptions are to be regarded as illustrative in nature and not restrictive.

DETAILED DESCRIPTION

Figure 1A:
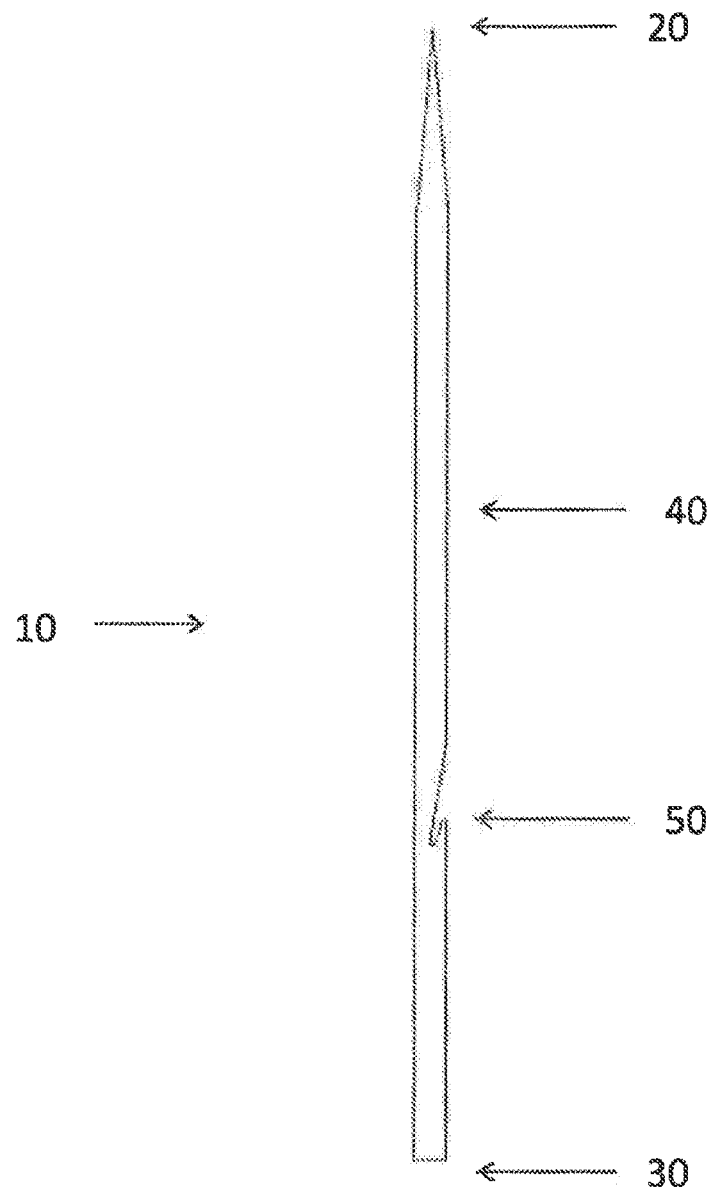
FIG. 1. An illustration of a locking needle that includes a graduated groove is provided.
FIG. 1B shows the locking needle of FIG. 1A with a ridge.
FIG. 1C shows the locking needle of FIG. 1A with a notch.
FIG. 1D shows the locking needle of FIG. 1A with a T-shaped locking groove.
FIG. 1E shows the locking needle of FIG. 1A with an L-shaped locking groove.
FIG. 1F shows the locking needle of FIG. 1A with a V-shaped locking groove.
FIG. 1G shows the locking needle of FIG. 1A with a U-shaped locking groove.
FIG. 1H shows the locking needle of FIG. 1A with a graduated locking groove.

In the specification and in the claims, the terms "including" and "comprising" are open-ended terms and should be interpreted to mean "including, but not limited to . . . " These terms encompass the more restrictive terms "consisting essentially of" and "consisting of."

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", "characterized by" and "having" can be used interchangeably.

Unless defined otherwise, all technical and scientific terms used herein have the same meanings as commonly understood by one of ordinary skill in the art to which this invention belongs. All publications and patents specifically mentioned herein are incorporated by reference in their entirety for all purposes including describing and disclosing the chemicals, instruments, statistical analyses and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

A discovery has been made that solves problems associated with penile prosthesis implantation. The present disclosure provides a locking needle for use in a Furlow insertion tool during implantation of a penile prosthesis. It is envisioned without limitation, that the locking needle, surgical tool, and methods disclosed herein can be used for the implantation of Coloplast's male urology products including, for example, Titan®, Genesis®, Alpha I®, Excel™, and Mark II® penile implants for the treatment of erectile dysfunction. It is also envisioned that the locking needle, surgical tool, and methods disclosed herein can be used for the implantation of other brands of penile prosthetics including Promedon-Tube® (Cordoba, Argentina); Silimed® prosthesis (Rio de Janerio, Brazil); Jonas® prosthesis by Bard Co. (Murray Hill, N.J., USA); Virilis I™ and Virilis II™ prostheses by Giant Medical (Cremona, Italy); Apollo™ prosthesis by Giant Medical Corporation (Cremona, Italy); AMS 600™, AMS 650™, Dura II™, Ambicor®, and AMS 700™ series 700 CX, Ultrex, and CXR by American Medical Systems (Minnetonka, Minn., USA). Both inflatable and non-inflatable semirigid penile implants can be used.

In a single embodiment the disclosure provides a locking needle for the implementation of a penile prosthesis. In another embodiment, a surgical tool for the implementation of a penile prosthesis, the surgical tool comprising a Furlow insertion tool and a locking needle adapted for insertion into the Furlow insertion tool, wherein the needle contains a graduated groove, and wherein a continuous suture loop can engage and lock into the graduated groove of the needle. The disclosure thereby eliminates the need to thread two suture ends through a Keith needle and fumbling with the suture ends during surgery.

The Furlow insertion tool of U.S. Pat. No. 4,244,370 is incorporated here within by reference in its entirety. The Furlow insertion tool includes a hollow barrel having an obturator slidably mounted therein and having a rounded forward end. A locating device is attached to the barrel to stabilize the obturator in the plurality of predetermined positions as it is moved along the bore of the barrel. A needle having suture material attached may be placed within the bore of the barrel. A slot is located along the length of the barrel to allow the suture material to exit from the side of the barrel. In practice, the tool may be inserted into a bodily structure such as one of the corpora cavernosa of a penis. The outer surface of the barrel is equipped with a plurality of markings that allow the user to gauge the depth that the barrel has been inserted into a bodily structure. After the tool is inserted, the obturator is slid along the barrel bore to force the needle out of the rounded forward end of the barrel. The needle is manually pulled out of the bodily structure. After the tool is withdrawn, suture material remains threaded through the bodily structure.

The Furlow insertion tool of the current embodiments is adapted for use with the a locking needle. The locking needle fits within the barrel bore of the Furlow insertion tool and is ejected from the forward end by manipulation of the obturator. The bore of the Furlow insertion tool has such a diameter that the locking needle is adapted to be disposed within the bore and ejected without undesired resistance.

Figure 1B:
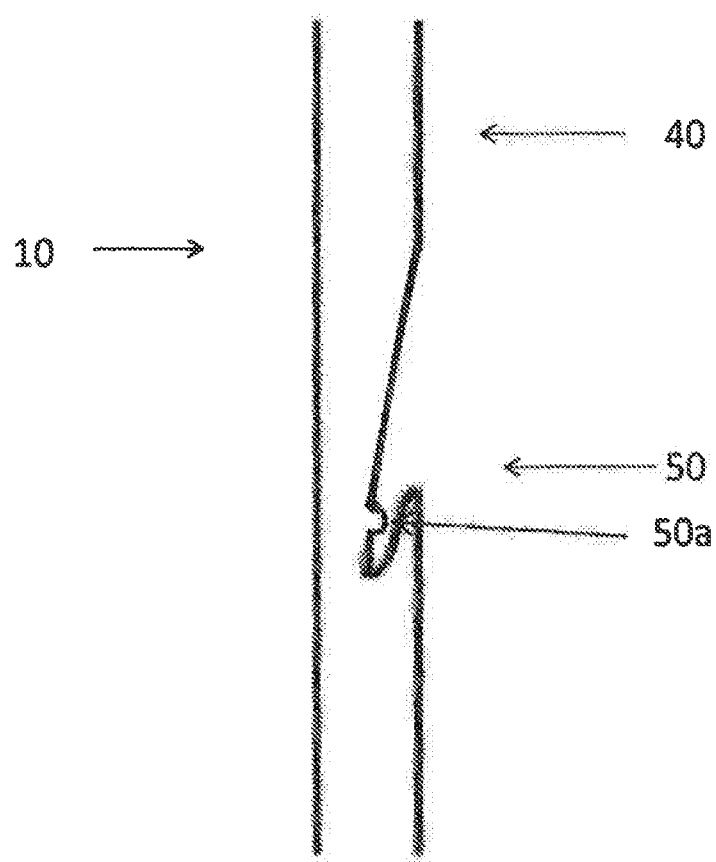
Figure 1C:
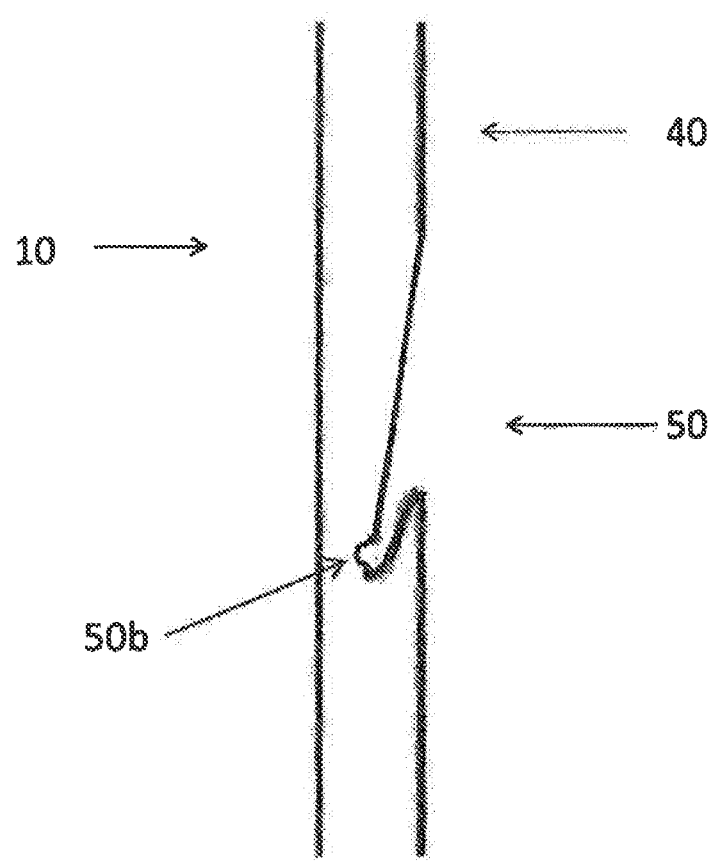
Figure 1D:
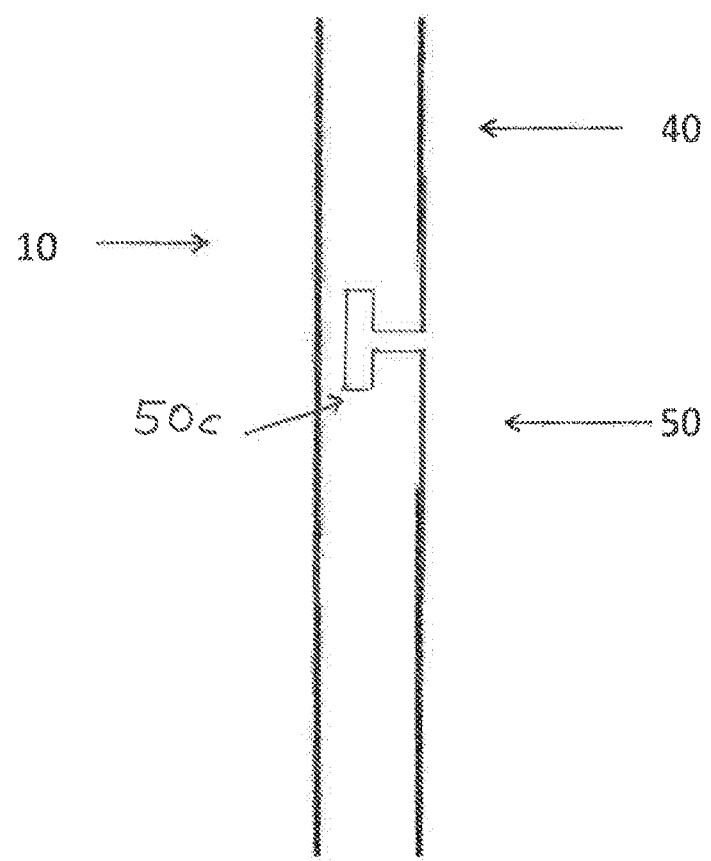
Figure 1E:
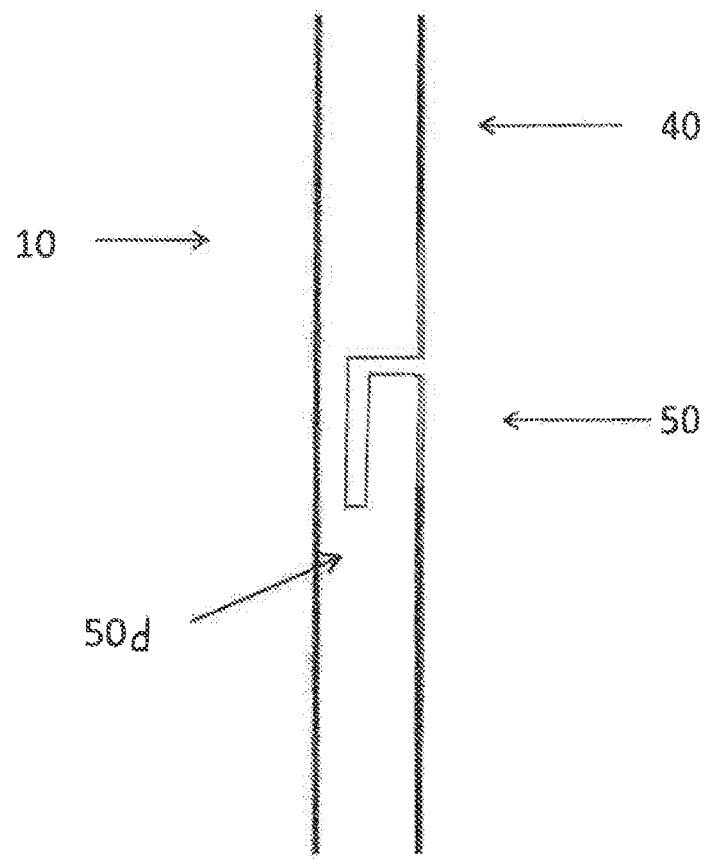
Figure 1F:
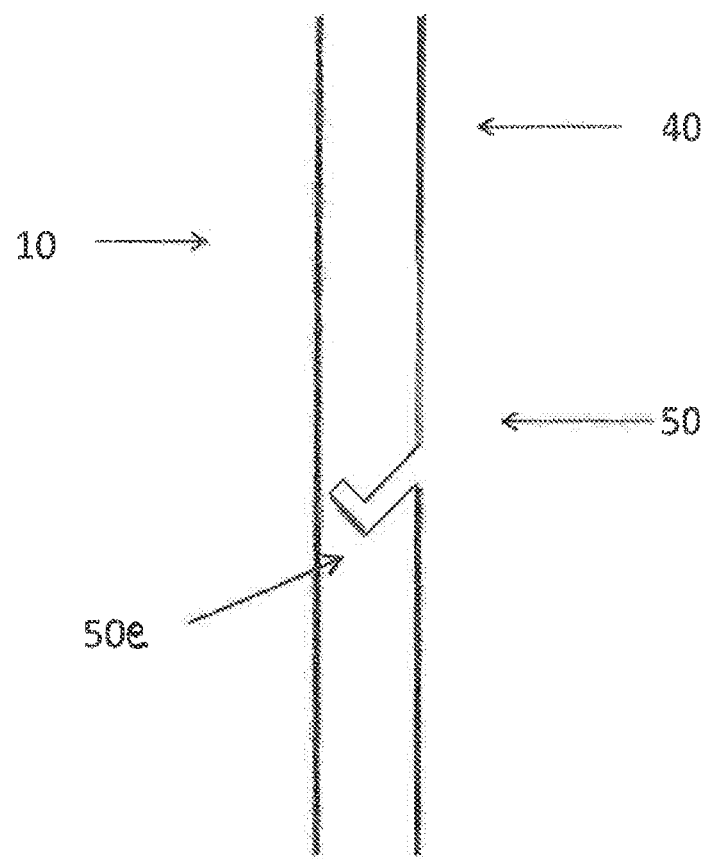
Figure 1G:
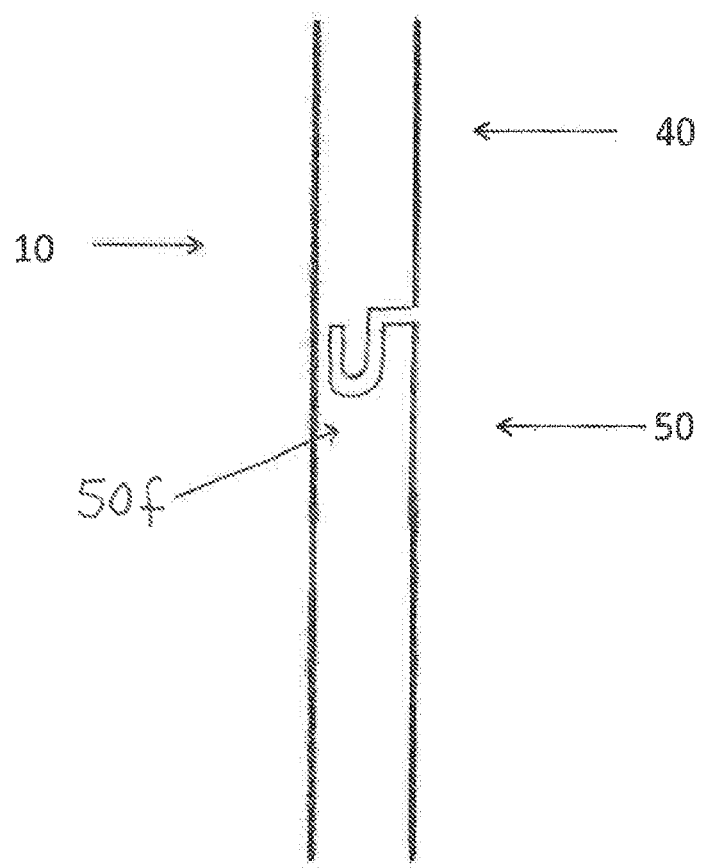

Referring to FIG. 1A, an illustration of the locking needle including a graduated groove used with a Furlow insertion tool is described. In FIG. 1A, locking needle 10 includes shaft 40 with tip 20 and end 30 having graduated groove 50 along shaft 40. Graduated groove 50 can be located along shaft 40 near tip 20, near end 30, or anywhere in between. The depth and size of graduated groove 50 is appropriate to engage a strand or strands of one or more sutures. In some non-limiting embodiments, graduated grove 50 is graduated and includes an additional ridge 50a (FIG. 1B) or notch 50b (FIG. 1C) within the groove 50 to help secure or lock an incoming suture or sutures. In another aspect, graduated groove 50 can have a T-shape, L-shape, V-shape, or U-shape.

Figure 2:
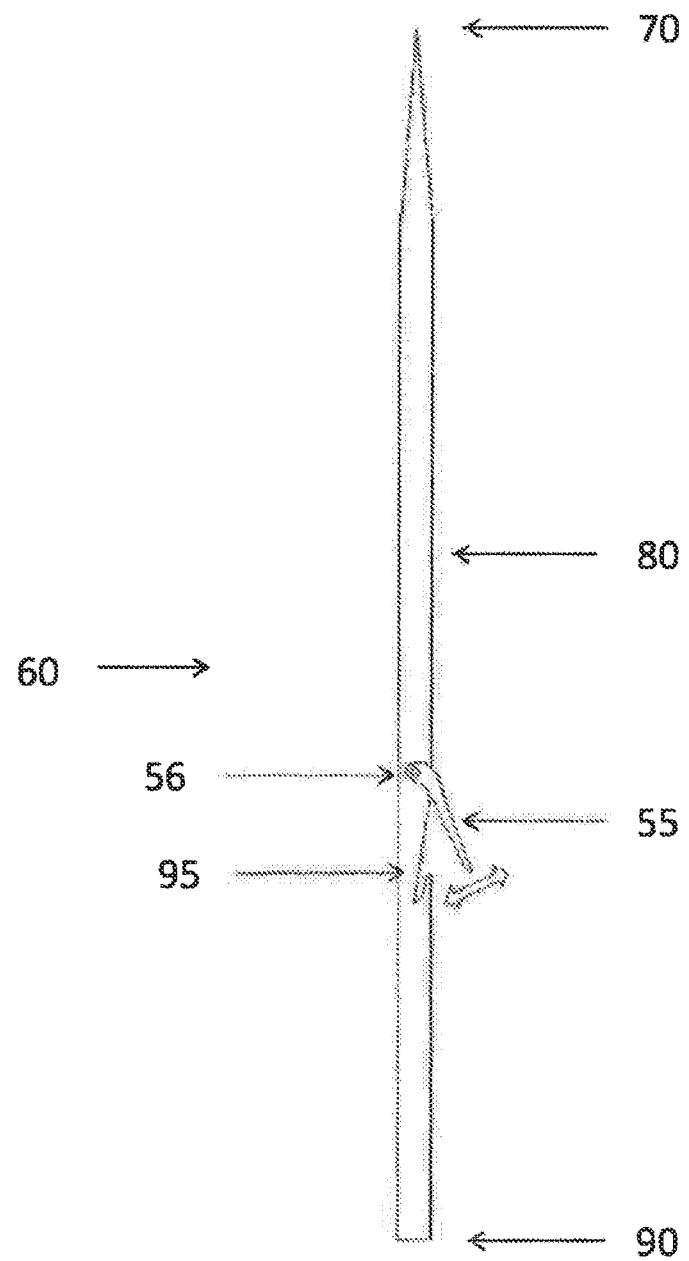
FIG. 2. An illustration of a locking needle that includes a graduated groove and rearward closing gate is provided.

Referring to FIG. 2, an illustration of the locking needle including a graduated groove and a rearward opening gate used with a Furlow insertion tool is described. In FIG. 2, locking needle 60 contains rearward opening gate 55 attached to shaft 80 by hinge 56. Rearward opening gate 55 may be fitted to snap or secure onto shaft 80 or can be spring loaded to enclose and lock a suture within graduated groove 95 of needle 60. In another aspect, rearward opening gate 55 may also be positioned inside graduated groove 50 and have a latching mechanism like that of a carabineer. Graduated groove 50 and corresponding rearward opening gate 55 of locking needle 60 can be located along shaft 80 near tip 70, near end 90, or anywhere in between.

Figure 3:
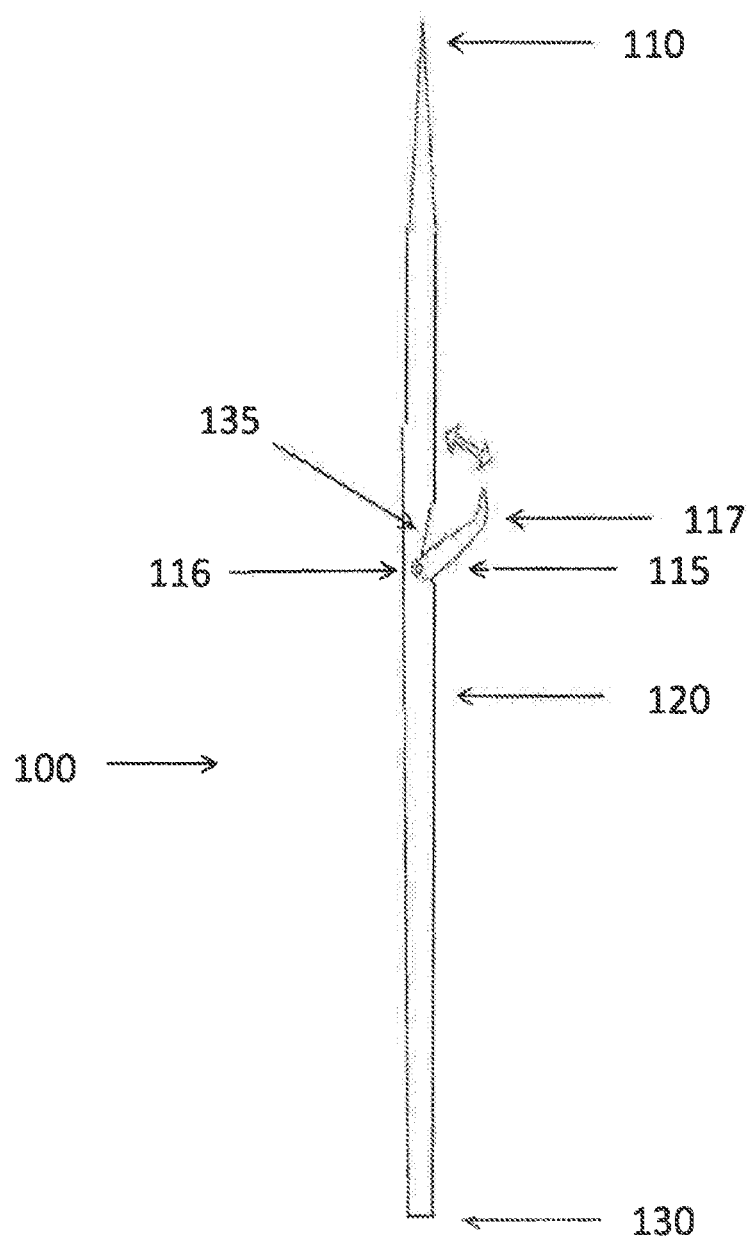
FIG. 3. An illustration of a locking needle that includes a graduated groove and a forward closing gate is provided.

Referring to FIG. 3, an illustration of the locking needle including a graduated groove and a forward opening gate used with a Furlow insertion tool is described. In FIG. 2, locking needle 100 includes shaft 120 with tip 110 and end 130 with forward opening gate 115 attached to shaft 120 by hinge 116. Forward opening gate 115 may be fitted to snap or secure onto shaft 120 or can be spring loaded to enclose and lock a suture within graduated groove 135 of needle 100. Forward opening gate 115 can have a curved or hooked shaped tip 117. Curved or hooked shaped tip 117 can be forked or shaped any way appropriately to fit securely to shaft 120 It is envisioned that having forward opening gate 115 will permit locking needle 100 to be preloaded into a Furlow insertion tool and curved or hooked shaped tip 117 will allow easy lassoing of a suture or sutures by the surgeon. Preloaded locking needle 100 will also speed up the prosthesis procedure and eliminate unnecessary handing of locking needle 100. Graduated groove 135 and corresponding forward opening gate 115 of locking needle 100 can be located anywhere along shaft 120, but preferably near tip 110.

Figure 4:
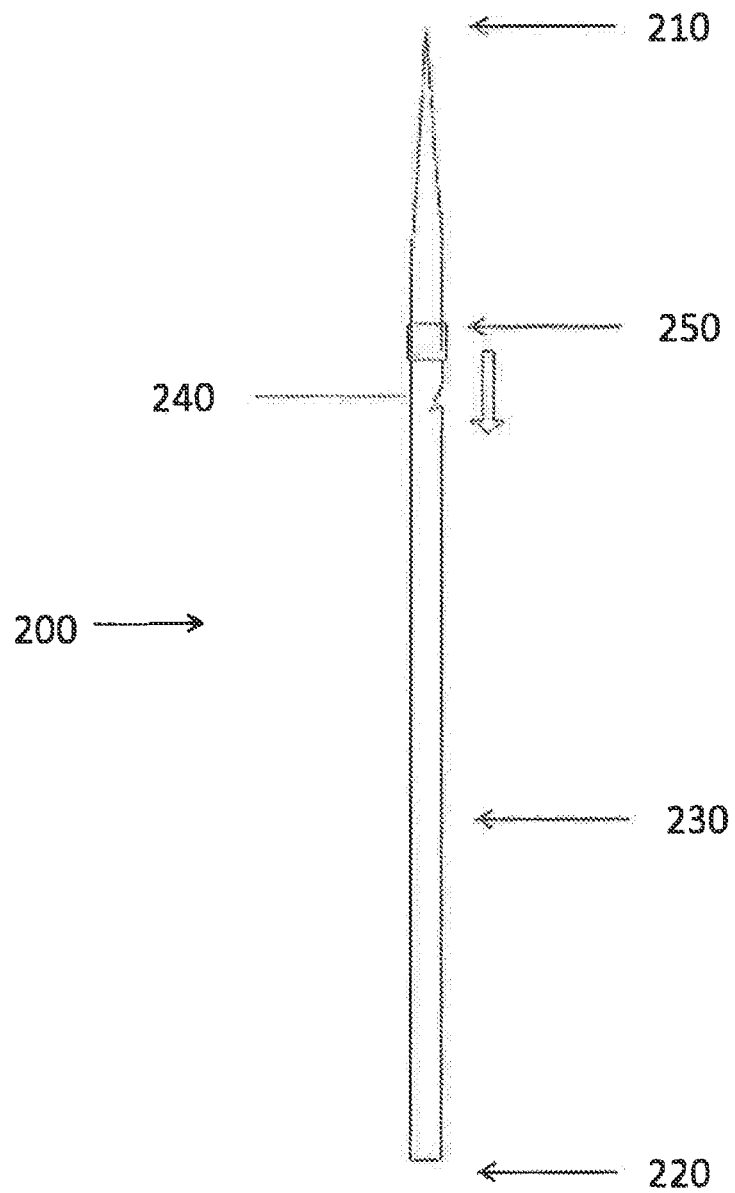
FIG. 4. An illustration of a locking needle that includes a graduated groove and a sleeve is provided.

Referring to FIG. 4, an illustration of the locking needle including a graduated groove and a sleeve used with a Furlow insertion tool is described. In FIG. 4, locking needle 200 includes shaft 230 with tip 210 and end 220. Sleeve 250 can be slid along shaft 230 to lock a suture or sutures with graduated groove 240. Sleeve can be detachable and constitute any suitable medical material and function as readily apparent to those skilled in the art, in view of the present disclosure.

The piercing point of the tips 20, 70, 110, 210 of locking needles 10, 60, 100, 200 can be tapered, tapered triangular (tricut), trocar, tapercut, or chiseled. The blunt ends 30, 90, 130, 220 of locking needles 10, 60, 100, 200 can be flat or rounded.

Locking needles 10, 60, 100, 200 comprises a surgical stainless steel which includes grades of stainless steel that are used in biomedical applications. The most common surgical steels are austenitic 316 stainless and martensitic 440 and 420 stainless steels. However the stainless steel can be any grade of corrosion resistant steel. Commonly 316 stainless steel, also referred to as "Marine Grade Stainless Steel", is a chromium, nickel, molybdenum alloy of steel that exhibits relatively good strength and corrosion resistance. 440 and 420 stainless steels, known also by the name "Cutlery Stainless Steel", are high carbon steels alloyed with chromium that have very good corrosion resistance compared to other cutlery steels, but their corrosion resistance is inferior to 316 stainless. Biomedical cutting instruments are often made from 440 or 420 stainless due to its high hardness coupled with acceptable corrosion resistance.

Locking needles 10, 60, 100, 200 may comprise at least chromium, nickel, or molybdenum, and combinations thereof. Other metals and alloys commonly used as biomaterials are gold (Au), cobalt-chrome alloys (CoCr), titanium and titanium alloys (TiNi, Ti-6Al-4V, Ti—Al—V, Ti—Al—Mo, Ti—Al—Cr, Ti—Al—Cr—Co, Ti—Al—Nb, Ti—Zr—Al) and silver-mercury alloys (AgHg). Titanium alloys may contain alpha stabilizers (aluminium, gallium, germanium, carbon, oxygen and nitrogen) or beta stabilizers (molybdenum, vanadium, tantalum, niobium, manganese, iron, chromium, cobalt, nickel, copper and silicon). Of the number of titanium alloys known, Ti-6Al-4V is most commonly employed, however Ti-6Al-6Nb shows even greater strength and resistance to corrosion.

Figure 5:
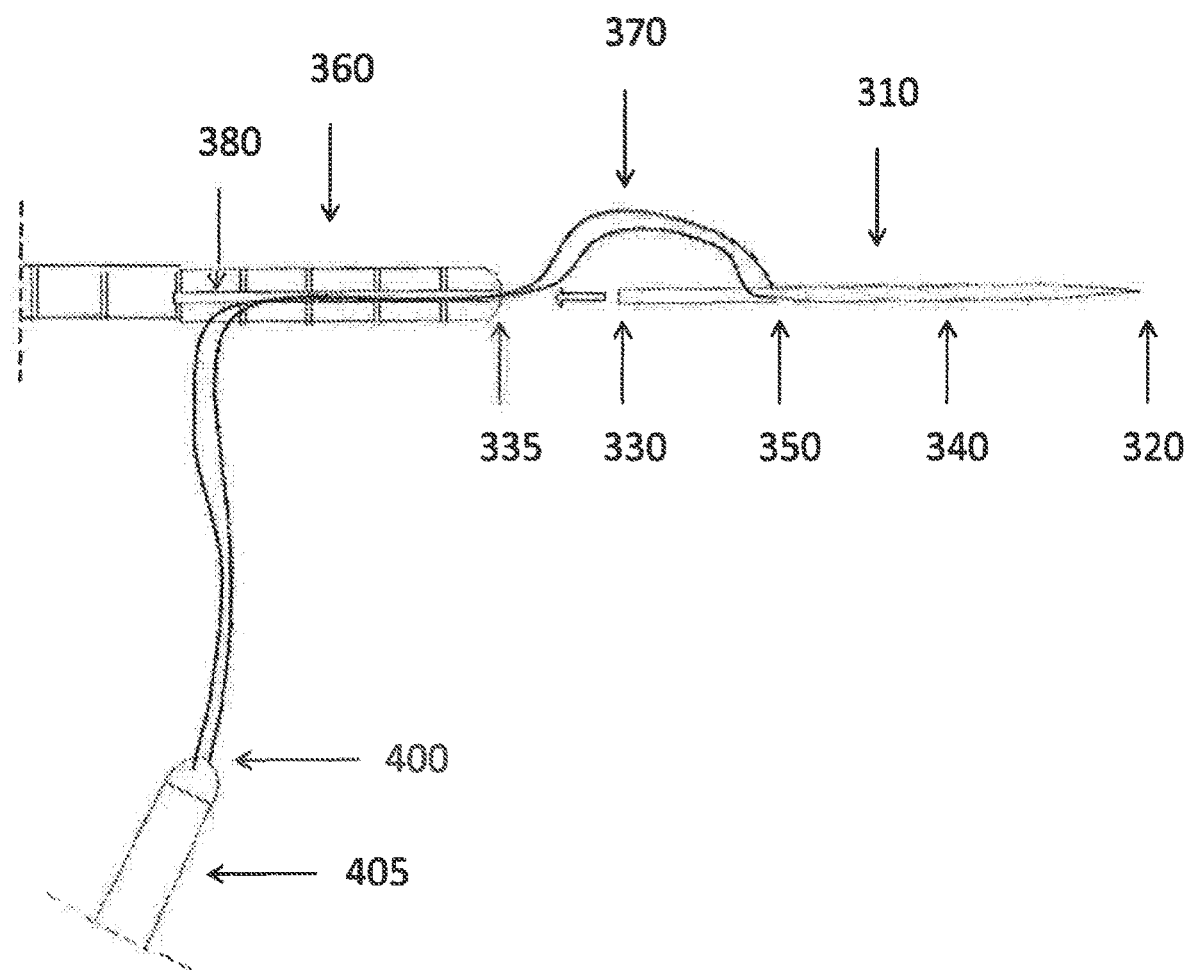
FIG. 5. An illustration of a continuous suture that is looped through an implantable medical device and a locking needle as described herein is provided. The locking needle is inserted into the barrel of a Furlow insertion tool prior to the time when the Furlow insertion tool is inserted into a corpus cavernosum.

Referring to FIG. 5, an illustration of the surgical tool comprising a locking needle and a Furlow insertion tool is described. In FIG. 2, continuous suture loop 370 is looped through distal end 400 of implantable cylinder 405 and graduated groove 350 of locking needle 310. FIG. 2 also depicts locking needle 310 being inserted into forward end 335 of Furlow insertion tool 360 prior to insertion of Furlow insertion tool 360 into the corpus cavernosum. Only part of Furlow insertion tool 360 and implantable cylinder 405 are shown in FIG. 5.

Continuous suture loop 370 comprises a continuous loop wherein the two free ends of a suture are fastened together to form a continuous loop to include implantable cylinder 405 at distal end 400. The suture is then stretched to form a longitudinal strand and the other end is lassoed to graduated groove 350 of locking needle 310. There is no particular limitation on the locking mechanism of locking needle 310 as part of the surgical tool. Locking needle 310 can secure continuous suture loop 370 by the use of a detachable sleeve, a forward or rearward opening gate, and/or by a ridge or notch within graduated groove 350. A surgeon can hold locking needle 310 in one hand including tethered continuous suture loop 370 and implantable cylinder 405. The surgeon can use the free hand to grasp Furlow 60 and slide locking needle 310 into the barrel (not shown) at forward end 335 of Furlow insertion tool 360 having continuous suture loop 370 pass through barrel slot 380. Locking needle 310 can be pulled into place using continuous suture loop 370 and can fit snuggly due to friction between continuous suture loop 370 and locking needle 310 within the barrel of Furlow insertion tool 360.

After locking needle 310 has been inserted into the barrel of Furlow insertion tool 360, it is ready for insertion in a body cavity. The surgical tool contemplated herein can be used for the implantation of an inflatable prosthesis into the corpora cavernosa of a penis. Herein a Furlow insertion tool 360 may be used for the implementation of a penile prosthesis, comprising a locking needle 310 adapted for insertion into the Furlow insertion tool 360, wherein the needle contains a graduated groove 350, and wherein a continuous suture loop 370 can engage the graduated groove 360 of the locking needle 310, thereby eliminating the need to thread two suture ends through a Keith needle and fumbling with the suture ends during surgery.

After Furlow insertion tool 360 is fully inserted into the corpus cavernosum and locking needle 310 is plunged out of the bore of the barrel of Furlow insertion tool 360 through the glans of the penis, locking needle 310 is then manipulated by the surgeon from outside the body and pulled from the penis. Furlow insertion tool 360 can then be withdrawn from the corpus cavernosum and implantable cylinder 405 pulled into place by continuous suture loop 370. Continuous suture loop 370 can then be cut and one strand pulled from the glans removing entire cut continuous suture loop 370. The above described procedure may be repeated to insert a second implant in the second corpora cavernosum.

In another embodiment the surgical tool can be used with a preloaded locking needle having a forward opening gate. The forward opening gate permits the lassoing of the suture without unnecessary handling of the locking needle for insertion into the surgical tool. Once the suture is lassoed around the locking needle the forward opening gate is then closed securing the suture to the locking needle. It is plausible that the locking needle with the forward opening gate may not require a groove as the suture may be sufficiently secured to the locking needle within the closed forward opening gate. In this aspect, the locking needle will have a lesser risk of contamination and the time of the prosthesis procedure will be shortened.

Applicant anticipates that the locking needle and surgical tool described herein may be used for such other medical purposes as surgically relocating body organs, particularly for the purpose of repositioning testicles.

Kits are also contemplated as being used in certain aspects of the invention. For instance, the locking needle or surgical tool of the present invention can be included in a kit. A kit can include a container. Containers can include a case, sachet, pouch, package, compartment or other containers into which the surgical tool is retained. The kit can include indicia on its surface. The indicia, for example, can be a word, a phrase, an abbreviation, a picture, or a symbol. A kit can also include instructions for using the kit, locking needle and/or surgical tool.

Further, the locking needle or surgical tool of the present invention may also be sterile, and the kits containing such tools can be used to preserve the sterility. The surgical tools may be sterilized via an aseptic manufacturing process or sterilized after packaging by methods known in the art.

The following paragraphs enumerated consecutively from 1 through 33 provide for various aspects of the present invention. In one embodiment, in a first paragraph (1), the present invention provides:

A needle, wherein the needle comprises a locking groove within the shaft of the needle.

2. The needle according to paragraph 1, wherein the locking groove of the shaft of the needle is graduated.

3. The needle according to paragraph 2, wherein a continuous suture loop is locked within the graduated locking groove of the shaft of the needle.

4. The needle according to paragraph 3, wherein the continuous suture loop further comprises a penile prosthesis cylinder.

5. The needle according to any of paragraphs 1 through 3, wherein the locking groove further comprises a ridge or notch.

6. The needle according to any of paragraphs 1 through 3, wherein the locking groove further comprises a rearward opening gate.

7. The needle according to any of paragraphs 1 through 3, wherein the locking groove further comprises a forward opening gate.

8. The needle according to paragraph 7, wherein the forward opening gate further comprises a curved or hooked tip.

9. The needle according to paragraph 1, wherein the needle further comprises a sleeve that slidably fits over the shaft of the needle.

10. The needle according to any of paragraphs 1 through 9, wherein the needle comprises an alloy including titanium, chromium, nickel, cobalt, molybdenum, or combinations thereof.

11. The surgical tool according to paragraph 10, wherein the alloy further comprises a stabilizer including aluminum, gallium, germanium, carbon, oxygen, nitrogen, molybdenum, vanadium, tantalum, niobium, manganese, iron, chromium, cobalt, nickel, copper, silicon, or combinations thereof.

12. The needle according to paragraph 4, wherein the needle is used during the implantation of a penile prosthesis cylinder.

13. A surgical tool for the implementation of a penile prosthesis, comprising a Furlow insertion tool and a needle adapted for insertion into the Furlow insertion tool, wherein the needle contains a locking groove along the shaft of the needle.

14. The surgical tool according to paragraph 13, wherein the locking groove of the needle is graduated from a wide opening to a narrow opening that can be V like in structure.

15. The surgical tool according to paragraph 14, wherein a continuous suture loop is locked within the graduated locking groove of the needle.

16. The surgical tool according to paragraph 15, wherein the continuous suture loop further comprises a penile prosthesis cylinder.

17. The surgical tool according to paragraph 13, wherein the locking groove further comprises a ridge or notch.

18. The surgical tool according to paragraph 13, wherein the locking groove further comprises a rearward opening gate.

19. The surgical tool according to paragraph 13, wherein the locking groove further comprises a forward opening gate.

20. The surgical tool according to paragraph 19, wherein the forward opening gate further comprises a curved or hooked tip.

21. The surgical tool according to paragraph 13, wherein the needle further comprises a sleeve that is slidably attached to the shaft of the needle that can cover the graduated groove in the shaft of the needle to help secure a suture.

22. The surgical tool according to any of paragraphs 13 through 21, wherein the needle comprises an alloy including titanium, chromium, nickel, cobalt, molybdenum, or combinations thereof.

23. The surgical tool according to paragraph 22, wherein the alloy further comprises a stabilizer including aluminum, gallium, germanium, carbon, oxygen, nitrogen, molybdenum, vanadium, tantalum, niobium, manganese, iron, chromium, cobalt, nickel, copper, silicon, or combinations thereof.

24. The surgical tool according to paragraph 16, wherein the surgical tool is used during the implantation of a penile prosthesis cylinder.

25. A method to implant a cylinder during penile prosthesis implementation using a locking needle, the method comprising:
(a) threading a suture through the distal end of the cylinder and securing the two ends of the suture together to form a continuous suture loop;
(b) securing the continuous suture loop to the locking needle, wherein the locking needle has a groove along a portion of the shaft of the needle;
(c) inserting the locking needle into a Furlow insertion tool;
(d) inserting the Furlow insertion tool containing the locking needle into the corpus cavernosum;
(e) positioning the locking needle through the glans of the penis and withdrawing the Furlow insertion tool from the corpus cavernosum;
(f) manipulating the locking needle and continuous suture loop and pulling the cylinder into the corpus cavernosum; and
(g) cutting the continuous suture loop and removing the cut suture from the glans of the penis.

26. The method according to paragraph 25, wherein step (b) and step (c) are reversed and the Furlow insertion tool is preloaded with the locking needle.

27. A method to implant a cylinder during penile prosthesis using the surgical tool of paragraph 13, the method comprising:
(a) threading a suture through the distal end of the cylinder and securing the two ends of the suture together to form a continuous suture loop;
(b) securing the continuous suture loop to the locking needle;
(c) inserting the locking needle into a Furlow insertion tool;
(d) inserting the surgical tool into the corpus cavernosum;
(e) positioning the locking needle through the glans of the penis and withdrawing the Furlow insertion tool from the corpus cavernosum;
(f) manipulating the locking needle and continuous suture loop and pulling the cylinder into the corpus cavernosum; and
(g) cutting the continuous suture loop and removing the cut suture from the glans of the penis.

28. The method according to paragraph 27 omitting step (c), wherein the surgical tool is preloaded with the locking needle.

29. The method according to paragraph 28, wherein the locking needle of the preloaded surgical tool comprises a forward opening gate.

30. A kit to implant a penile prosthesis cylinder, the kit comprising:
(a) the locking needle of any of paragraphs 1 through 12; and
(b) instructions for using the locking needle.

31. The kit according to paragraph 30, wherein the kit further comprises sutures.

32. A kit to implant an penile prosthesis cylinder using the surgical tool of any of paragraphs 13 through 24, the kit comprising:
(a) a Furlow insertion tool;
(b) the locking needle; and
(c) instructions for using the kit and/or surgical tool.

33. The kit according to paragraph 32, wherein the kit further comprises sutures.

The above description is given by way of example, and not limitation. Given the above disclosure, one skilled in the art could devise variations that are within the scope and spirit of the invention disclosed herein, including various ways of surgically implanting the implants described herein. Further, the various features of the embodiments disclosed herein can be used alone, or in varying combinations with each other and are not intended to be limited to the specific combination described herein. Thus, the scope of the claims is not to be limited by the illustrated embodiments.

The invention claimed is:

1. A method of implanting a penile prosthesis, the method comprising:
providing a tool including a needle having a locking groove formed in a shaft of the needle, where the locking groove comprises one of a ridge and a notch;
accessing a penile implant having a length of suture coupled to a distal end of the penile implant;
securing the length of suture into the locking groove of the needle;
inserting the tool and the needle into a corpora cavernosum of a penis;
passing the needle and the length of suture through a glans of the penis;
disengaging the length of suture from the locking groove of the needle; and
pulling the penile implant into the corpora cavernosum of the penis with the length of suture.

2. The method of claim 1, comprising inserting the needle into tool.

3. The method of claim 1, comprising providing the tool including a preloaded needle inserted into the tool.

4. The method of claim 1, comprising securing the length of suture into the ridge of the locking groove of the needle.

5. The method of claim 1, comprising securing the length of suture into the notch of the locking groove of the needle.

6. The method of claim 1, further comprising providing the tool with a bore and an obturator insertable into the bore; and
moving the obturator within the bore and pushing the needle out of the bore and through the glans of the penis.

7. The method of claim 1, further comprising providing the tool with a bore, an obturator insertable into the bore, and a preloaded needle retained within the bore of the tool; and
moving the obturator within the bore and pushing the preloaded needle out of the bore of the tool and through the glans of the penis.

8. The method of claim 1, further comprising tying together two ends of the length of suture and forming a continuous loop in the length of suture, and securing the continuous loop of the length of suture into the locking groove of the needle.

9. The method of claim 1, further comprising sliding a sleeve relative to the shaft of the needle and exposing the locking groove formed in the shaft of the needle.

10. The method of claim 1, further comprising sliding a sleeve forward in a distal direction relative to the shaft of the needle and exposing the locking groove formed in the shaft of the needle.

11. The method of claim 1, further comprising sliding a sleeve rearward in a proximal direction relative to the shaft of the needle and exposing the locking groove formed in the shaft of the needle.

12. The method of claim 1, further comprising opening a gate on the needle and exposing the locking groove formed in the shaft of the needle.

13. The method of claim 1, further comprising disengaging the length of suture from the locking groove of the needle by cutting the suture and manually removing the needle from the suture.

14. The method of claim 1, comprising providing the tool including the needle having a T-shaped locking groove formed in the shaft of the needle, and securing the length of suture into the T-shaped locking groove of the needle.

15. The method of claim 1, comprising providing the tool including the needle having a L-shaped locking groove formed in the shaft of the needle, and securing the length of suture into the L-shaped locking groove of the needle.

16. The method of claim 1, comprising providing the tool including the needle having a V-shaped locking groove formed in the shaft of the needle, and securing the length of suture into the V-shaped locking groove of the needle.

17. The method of claim 1, comprising providing the tool including the needle having a U-shaped locking groove formed in the shaft of the needle, and securing the length of suture into the U-shaped locking groove of the needle.

18. The method of claim 1, comprising providing the tool including the needle having a graduated locking groove formed in the shaft of the needle, and securing the length of suture into the graduated locking groove of the needle.

* * * * *